(12) United States Patent
Williams

(10) Patent No.: US 10,058,667 B2
(45) Date of Patent: *Aug. 28, 2018

(54) PORTABLE MANUAL VENTILATION DEVICE

(71) Applicant: Osborne Williams, Dix Hills, NY (US)

(72) Inventor: Osborne Williams, Dix Hills, NY (US)

( * ) Notice: Subject to any disclaimer, the term of this patent is extended or adjusted under 35 U.S.C. 154(b) by 244 days.

This patent is subject to a terminal disclaimer.

(21) Appl. No.: 14/851,292

(22) Filed: Sep. 11, 2015

(65) Prior Publication Data

US 2016/0001025 A1    Jan. 7, 2016

Related U.S. Application Data

(60) Continuation of application No. 14/606,478, filed on Jan. 27, 2015, now Pat. No. 9,604,022, and a division (Continued)

(51) Int. Cl.
*A61M 16/08* (2006.01)
*A61M 16/00* (2006.01)
(Continued)

(52) U.S. Cl.
CPC .... *A61M 16/0078* (2013.01); *A61M 16/0003* (2014.02); *A61M 16/0051* (2013.01);
(Continued)

(58) Field of Classification Search
CPC ......... A61B 5/0002; A61B 5/01; A61B 5/082; A61B 5/0836; A61B 5/087; A61B 5/0876;
(Continued)

(56) References Cited

U.S. PATENT DOCUMENTS

| 3,556,097 A | 1/1971 | Wallace |
| 4,903,693 A | 2/1990 | Yasue |

(Continued)

FOREIGN PATENT DOCUMENTS

| WO | 19990062403 A1 | 12/1999 |
| WO | 2005050524 A2 | 6/2005 |

(Continued)

OTHER PUBLICATIONS

Anonymous, "Ambu® Products" Ambu website, www.ambu.com/corp/products/emergency_care/product/disposable_pressure_manonneter_prod860.aspx.

(Continued)

*Primary Examiner* — Annette Dixon
(74) *Attorney, Agent, or Firm* — Werschulz Patent Law, LLC; Patricia P. Werschulz, Esq.

(57) ABSTRACT

A portable, compact closed circuit ventilation device for manual ventilation of a patient undergoing a surgical or medical procedure that requires sedation as well as emergency management of respiratory failure. One example embodiment includes a closed breathing circuit having a manually squeezable bag, a carbon dioxide absorption canister, a plurality of valves, a gas port and a plurality of sensors for measuring Tidal Volume (TV), Peak Airway Pressure (PAP) and End Tidal CO2 (ETCO2). Another example embodiment includes an open breathing circuit having a bag, valves and sensors. A monitor displays the sensor measurements during the respiratory phases. In a spontaneously breathing patient the device may be used to assess the adequacy of patient's respiratory efforts. During manual or assisted ventilation, the monitor assures safe and efficacious ventilation by the closed breathing circuit.

18 Claims, 4 Drawing Sheets

Related U.S. Application Data of application No. 14/151,486, filed on Jan. 9, 2014, now Pat. No. 8,973,580.

(51) Int. Cl.

| | | |
|---|---|---|
| *A61M 16/22* | (2006.01) | |
| *A61M 16/20* | (2006.01) | |
| *A61M 16/10* | (2006.01) | |
| *A61M 16/04* | (2006.01) | |
| *A61M 16/06* | (2006.01) | |

(52) U.S. Cl.
CPC .... *A61M 16/0081* (2014.02); *A61M 16/0084* (2014.02); *A61M 16/021* (2017.08); *A61M 16/04* (2013.01); *A61M 16/06* (2013.01); *A61M 16/08* (2013.01); *A61M 16/0875* (2013.01); *A61M 16/0883* (2014.02); *A61M 16/0891* (2014.02); *A61M 16/104* (2013.01); *A61M 16/1005* (2014.02); *A61M 16/20* (2013.01); *A61M 16/201* (2014.02); *A61M 16/208* (2013.01); *A61M 16/22* (2013.01); *A61M 2016/0027* (2013.01); *A61M 2016/0033* (2013.01); *A61M 2016/103* (2013.01); *A61M 2202/0225* (2013.01); *A61M 2205/18* (2013.01); *A61M 2205/3327* (2013.01); *A61M 2205/3331* (2013.01); *A61M 2205/35* (2013.01); *A61M 2205/502* (2013.01); *A61M 2205/8206* (2013.01); *A61M 2230/432* (2013.01)

(58) Field of Classification Search
CPC ....... A61B 5/1106; A61B 5/162; A61B 5/411; A61B 5/417; A61B 5/4821; A61B 5/4836; A61B 5/74; A61M 15/02; A61M 16/00; A61M 16/0051; A61M 16/0075; A61M 16/0078; A61M 16/0081; A61M 16/0084; A61M 16/009; A61M 16/0093; A61M 16/01; A61M 16/04; A61M 16/06; A61M 16/0688; A61M 16/08; A61M 16/1015; A61M 16/104; A61M 16/12; A61M 16/18; A61M 16/202; A61M 16/208; A61M 16/209; A61M 16/22; A61M 19/00; A61M 2005/1405; A61M 2016/0021; A61M 2016/0027; A61M 2016/0033; A61M 2016/0036; A61M 2016/0039; A61M 2016/0042; A61M 2039/1005; A61M 2202/0208; A61M 2202/0291; A61M 2205/18; A61M 2205/276; A61M 2205/3303; A61M 2205/3324; A61M 2205/3368; A61M 2205/3379; A61M 2205/3561; A61M 2205/3592; A61M 2205/50; A61M 2205/502; A61M 2205/505; A61M 2205/52; A61M 2205/581; A61M 2205/583; A61M 2205/8206; A61M 2205/8212; A61M 2205/8237; A61M 2209/084; A61M 2230/205; A61M 2230/42; A61M 2230/43; A61M 2230/432; A61M 5/142; A61M 5/1723; G06F 19/3406; G06F 19/345; G06F 19/3456; G06F 19/3468; G06F 19/3481; G06Q 50/22; G06Q 50/24; Y10S 128/909; Y10S 128/911; Y10S 128/912; Y10T 428/24355; G09B 23/288
USPC ............ 128/200.24, 202.27, 203.12, 203.13, 128/203.14, 203.28, 204.18, 204.21, 128/204.23, 204.25, 205.12, 205.13, 128/205.14, 205.15, 205.17, 205.23, 128/205.24, 205.25, 206.21, 206.22, 128/206.24, 206.25, 909, 911, 912; 600/300, 301, 431, 529, 532, 533, 538, 600/541, 561; 604/65, 66

See application file for complete search history.

(56) References Cited

U.S. PATENT DOCUMENTS

| | | | |
|---|---|---|---|
| 5,694,924 | A | 12/1997 | Cewers |
| 7,172,557 | B1 | 2/2007 | Parker |
| 7,201,734 | B2 | 4/2007 | Hickle |
| 7,836,882 | B1 | 11/2010 | Rumph et al. |
| 8,267,081 | B2 | 9/2012 | Flanagan et al. |
| 8,312,877 | B2 | 11/2012 | Elaz et al. |
| 8,333,198 | B2 | 12/2012 | Sinha |
| 9,604,022 | B2 * | 3/2017 | Williams ............... A61M 16/22 |
| 2008/0053445 | A1 | 3/2008 | Kroupa et al. |
| 2009/0095300 | A1 | 4/2009 | McMorrow |
| 2010/0132706 | A1 | 6/2010 | Nashed |
| 2014/0275820 | A1 * | 9/2014 | Varga ................ A61M 16/0078 600/301 |

FOREIGN PATENT DOCUMENTS

| | | |
|---|---|---|
| WO | 2007096181 A1 | 8/2007 |
| WO | 2009121139 A1 | 10/2009 |
| WO | 2010096299 A1 | 8/2010 |
| WO | 2011094018 A2 | 8/2011 |

OTHER PUBLICATIONS

Anonymous, "Anethesia Workstations," Fabius Tiro website, www.draeger.com/sites/enus_us/Pages/Hospital/Fabius-Tiro.aspx.

Anonymous, "Resuscitimer" Allied Healthcare Products, Inc. website, www.alliedhpi.com/images/z90-00-0009.pdf.

Anonymous,"AMBU CO2 Detector," Emergency Medical Products, Inc. website, www.buyemp.com/product/ambu-co2-detector.

Eikaas, Henrik and Raeder, Johan, Total intravenous anaesthesia techniques for ambulatory surgery, Current Opinion in Anaesthesiology, 2009, pp. 725-729, vol. 22, Wolters Kuwer Health | Lippincott Williams & Wilkins, published online, http://journals.lww.com/co-anesthesiology/pages/default.aspx.

* cited by examiner

PORTABLE MANUAL VENTILATION DEVICE

CROSS-REFERENCE TO RELATED APPLICATIONS

This application is a continuation of the nonprovisional patent application Ser. No. 14/606,478, issued as U.S. Pat. No. 9,604,022 on Mar. 28, 2017, filed in the United States Patent Office on Jan. 27, 2015, which is a divisional application of the nonprovisional patent application Ser. No. 14/151,486, issued as U.S. Pat. No. 8,973,580 on Mar. 10, 2015, filed in the United States Patent Office on Jan. 9, 2014 and claims the priority thereof and is expressly incorporated herein by reference in its entirety.

TECHNICAL FIELD

The present disclosure relates generally to a medical ventilation device. More particularly, the present disclosure relates to a portable manual circuit ventilation device and system for use during medical procedures requiring anesthesia, as well as emergency management of respiratory failure.

BACKGROUND

The development of modern surgery began when doctors started administering anesthesia to the patients before and during surgical procedures. Anesthesia blocks or removes sensation particularly the feeling of pain, allowing the surgeon to perform surgery without patients experiencing extreme distress and pain they would otherwise undergo. Anesthesia produces a medically induced coma and a loss of protective reflexes from one or more medications resulting in amnesia, analgesia, muscle relaxation and sleep.

In standard operating rooms, an anesthesiologist administers general anesthesia through large machines that are connected to the patient's respiratory system. Drugs used to induce general anesthesia are administered through inhalation and/or injection. Most commonly, anesthesia is induced by injection and maintained through inhalation.

During general anesthesia, the patient is not breathing on his own, but through a closed system of the anesthesia machine. The most common type anesthesia machine is a continuous flow, which is designed to supply oxygen, anesthetic drug as a gas and ambient air to the patient. As a closed system, respiratory parameters are easily monitored. Not only is the amount of anesthetic drug accurately monitored, but also many parameters such as oxygen saturation, as well as inspired and expired gases. The anesthesia machine, because of its complexity, size and infrastructure requirements, is typically rooted to the traditional operating room.

Now many medical procedures, both surgical and nonsurgical, are performed outside the operating room in various hospital suites, ambulatory surgical suites and doctors' offices. Most procedures performed outside of a traditional operating room require an anesthesiologist to administer sedation, not general anesthesia. Generally, the sedating drugs are administered by injection and not by inhalation. Because no drugs are administered by inhalation, the anesthesia machine is not required and remains a fixture only in the traditional hospital operating room. The patient breathes on his own during the procedure.

Often the patient stops breathing and needs to be resuscitated with a bag-valve-mask, such as an AMBU® bag, (AMBU® is the registered trademark of AMBU A/S, Ballerup, Denmark) to start breathing again. The patient has been breathing on his own up to this point and the respiratory system is not coupled to any mechanical ventilation device.

The bag-valve-mask is the only tool available in most surgical suites and offices and it is very limited in function. The bag-valve-mask and valve is coupled to either a face mask secured to the patient's face or through an endotracheal tube. Ambient air is pushed into the lungs through a one-way valve when the bag is compressed by anesthesiologist or assistant. Once the bag has emptied into the lungs and released, it inflates from the other end and the air in the lungs is automatically expelled into ambient air, the bag-valve-mask constituting an open circuit system. The bag is compressed again for the next breath.

The amount and pressure of air entering the lungs is determined by the person compressing the bag. Generally bag-valve-masks are without any gauges, so only the experience and skill of the person compressing the bag protects the patient's lungs from over-inflating or over-pressurization. The person compressing the bag can only tell by external signs that the lungs are inflating properly, that air is not leaking from the mask or tracheal tube and the patient is properly being resuscitated.

The bag-valve-mask is further limited in mask ventilation situations when the patient has anatomic airway anomalies or is obese so that the mask does not fit tightly and seal around the nose and mouth. Without any gauges, the bag-valve-mask does not provide any objective method to assess adequacy of ventilation. In this situation, inadequate ventilation can lead to hypoxia and brain death.

While these units may be suitable for the particular purpose employed, or for general use, they would not be as suitable for the purposes of the present disclosure as disclosed hereafter.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

BRIEF SUMMARY

An aspect of an example embodiment in the present disclosure is to maximize patient safety during a surgical or medical procedure that requires sedation, but not general anesthesia. Accordingly, the present disclosure provides a portable, compact ventilation device for manual resuscitation that mounts on a wheeled stand for use in clinical applications where space is limited and only manual ventilation is available.

Another aspect of an example embodiment in the present disclosure is to provide superior sedation during a surgical or medical procedure that requires sedation, but not general anesthesia. According the present disclosure provides monitoring of ventilation quality so that optimal levels of sedation that do not endanger the patient but alleviate pain and maintain unconsciousness can be administered, producing superior sedation.

A further aspect of an example embodiment in the present disclosure is to provide a system where measurements of ventilation quality can be monitored during resuscitation. Accordingly, the present disclosure provides a breathing circuit, so that measurements of tidal volume, end tidal carbon dioxide concentration and peak airway pressure indicative of ventilation quality can be measured.

Accordingly, the present disclosure describes a portable, compact circuit ventilation device for manually ventilating a patient undergoing a surgical or medical procedure that requires sedation, but not general anesthesia, as well as emergency management of respiratory failure, in which only manual ventilation is available. The device includes a breathing circuit having a manually squeezable bag, a carbon dioxide absorption canister, a plurality of valves, a gas port, and a plurality of sensors for measuring TV (tidal volume), PAP (peak airway pressure) and ETCO2 (end tidal carbon dioxide). In one example embodiment, the device is a closed circuit having a carbon dioxide absorption canister. In one example embodiment, the device includes a monitor operative for displaying the measurement for each sensor as the squeezable bag is compressed, manually ventilating a patient, the monitor assuring safe and efficacious manual ventilation by the closed breathing circuit.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

Figure 1:
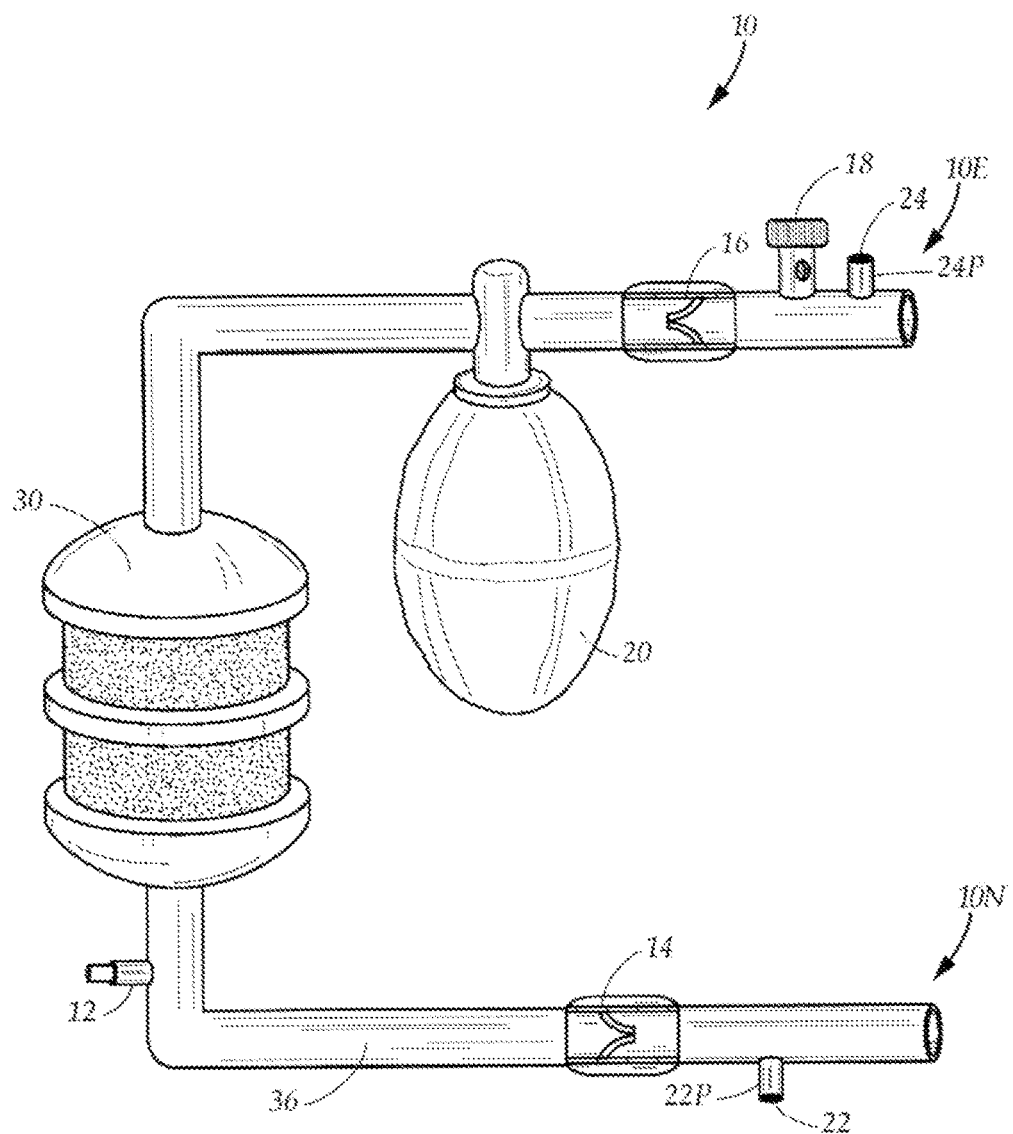
FIG. 1 is a perspective view of an example embodiment of a closed breathing circuit of a portable closed circuit ventilation device.

FIG. 1 illustrates a closed breathing circuit 10 of a portable closed circuit ventilation device for manually ventilating a patient. The portable closed circuit ventilation device is useful for clinical applications for patients who are undergoing surgical and medical procedures that require sedation, but not general anesthesia, as well as emergency management of respiratory failure throughout the hospital. The uniqueness of the described closed circuit device is in the small size, portability and is discrete and independent from other equipment. Structurally it is simpler and very different from the traditional anesthesia machine, allowing it to be used for very different applications and functions.

By clinical applications, reference is made to, but not limited to, same day surgical suites, either within a hospital campus or at an independent location, outpatient clinics and physicians' offices where patients undergo sedation. These procedures in clinical applications encompass surgery of many types, endoscopy, pain management, colonoscopy and other diagnostic procedures, as non-limiting examples. Additionally, the closed circuit ventilation device is useful for manually assisting ventilation by face mask before an endotracheal tube is inserted into the patient and secured.

In these clinical applications, traditional anesthesia machines are not practical nor cost effective for several reasons. These machines are designed for use in a traditional hospital operating room for drug delivery by inhalation. In order to regulate the dosage and rate of drug delivery, the patient's breathing is commonly machine-regulated and non-spontaneous, the machine continuously controlling the patient's breathing. The machines require highly trained specialists, are expensive to operate and require a large amount of space.

In clinical applications, medical personal depend on a bag-valve-mask in an open breathing circuit if resuscitation of the patient is required. In a standard open breathing circuit, the ability to measure a plurality of parameters such as, for example, not limited to, peak airway pressure (PAP), tidal volume (TV), and end tidal carbon dioxide concentration (ETCO2) is lacking. The standard open circuit that has the bag-valve-mask is not designed to measure these parameters.

FIG. 1 shows a closed breathing circuit of the device having a manually squeezable bag 20, a carbon dioxide absorption canister 30, a plurality of valves, namely an inspiratory valve 14, an expiratory valve 16, a valve 18 and a gas port 12 operative for allowing gases such as air and oxygen to be added to the closed breathing circuit as necessary. The bag 20, canister 30, the inspiratory valve 14, the expiratory valve 16, the valve 18 and port 12 are coupled by a tubing 36 and are in fluid communication within the closed breathing circuit 10. The closed breathing circuit 10 has an expiratory intersection 10E and inspiratory intersection 10N for connecting to a face mask on a patient, which is not shown. In another example embodiment, the expiratory intersection 10E and inspiratory intersection 10N are operative for connecting the closed breathing circuit 10, which in turn is operative for connecting via a face mask or artificial airway to the patient. Face masks and artificial airways are well-known to those of ordinary skill and further details are beyond the scope of the present disclosure.

The carbon dioxide absorption canister 30 is part of the closed breathing circuit 10 operative for preventing a buildup of excess carbon dioxide produced by the patient in the closed circuit to prevent hypercapnia. The canister contains a solid chemical compound with a high affinity for carbon dioxide, such as, as a non-limiting example, soda lime.

The bag 20 is for manual resuscitation when the device is in use. Ventilation is only in a manual mode. Respiration by a patient is either spontaneous and unassisted, or manual when spontaneous breathing is inadequate or ceases. The squeezable bag is manually pumped by the medical personal to resuscitate the patient, such that the gases in the system move only when the patient breathes or when the bag is squeezed. The squeezable bag can be, for example, a bag-valve-mask, a self-inflating bag, a soft non-self inflating bag or other types of resuscitation bags and the type of squeezable bag is not a limitation in the present disclosure.

In the example embodiment in FIG. 1, the closed breathing circuit 10 has a set of one-way valves, the expiratory valve 16, in proximity to the expiratory intersection 10E and the inspiratory valve 14, in proximity to the inspiratory intersection 10N that permit the flow of gases only in one direction. The closed breathing circuit 10 also has an adjustable pressure relief valve operative for maintaining pressure in the system operative to prevent over-inflating the patient's lungs causing volutrauma, by over stretching the lungs, barotrauma, by over pressuring the lungs and gastric insufflation.

The tubing 36 has an interior and in the interior is a plurality of sensors, namely a peak airway pressure sensor 22 inside port 22P and a flow tidal volume (TV) sensor inside port 24P, the sensors operative for measuring a plurality of parameters within the closed breathing circuit. A sensor is a device that measures a parameter and converts it into a signal, which can be read by the monitor. It is understood by those of ordinary skill that the sensors can be electrical, electronic, mechanical or biomechanical and that the type of sensor used is not a limitation of example embodiments presented herein. The sensors produce a measurement for the parameters associated with effective ventilation and resuscitation.

In the present example embodiment, the flow tidal volume (TV) sensor 24 is in proximity to the expiratory valve 16 and the expiratory intersection 10E, operative for measuring return tidal volume of expired gas from the patient, indicative of the effectiveness of the respiration. In proximity to the inspiratory valve 14 and the inspiratory intersection 10N, is the peak airway pressure sensor 22, indicating the peak airway pressure (PAP) operative for monitoring to prevent barotrauma, volutrauma and gastric insufflation. An additional sensor operative for measuring end tidal carbon dioxide concentration (ETCO2), operative for preventing hypercapnia is discussed hereinbelow.

In one example embodiment, the sensors are connected to wire leads to a power source and communicate measurements to a monitor described hereinbelow. In another example embodiment, the sensors are battery powered and communicate wirelessly to the monitor.

In one example embodiment, the closed breathing circuit 10 includes disposable, single use valves, ports, tubing, bag and canister operative for interfacing with the monitor described herein below.

Figure 4:
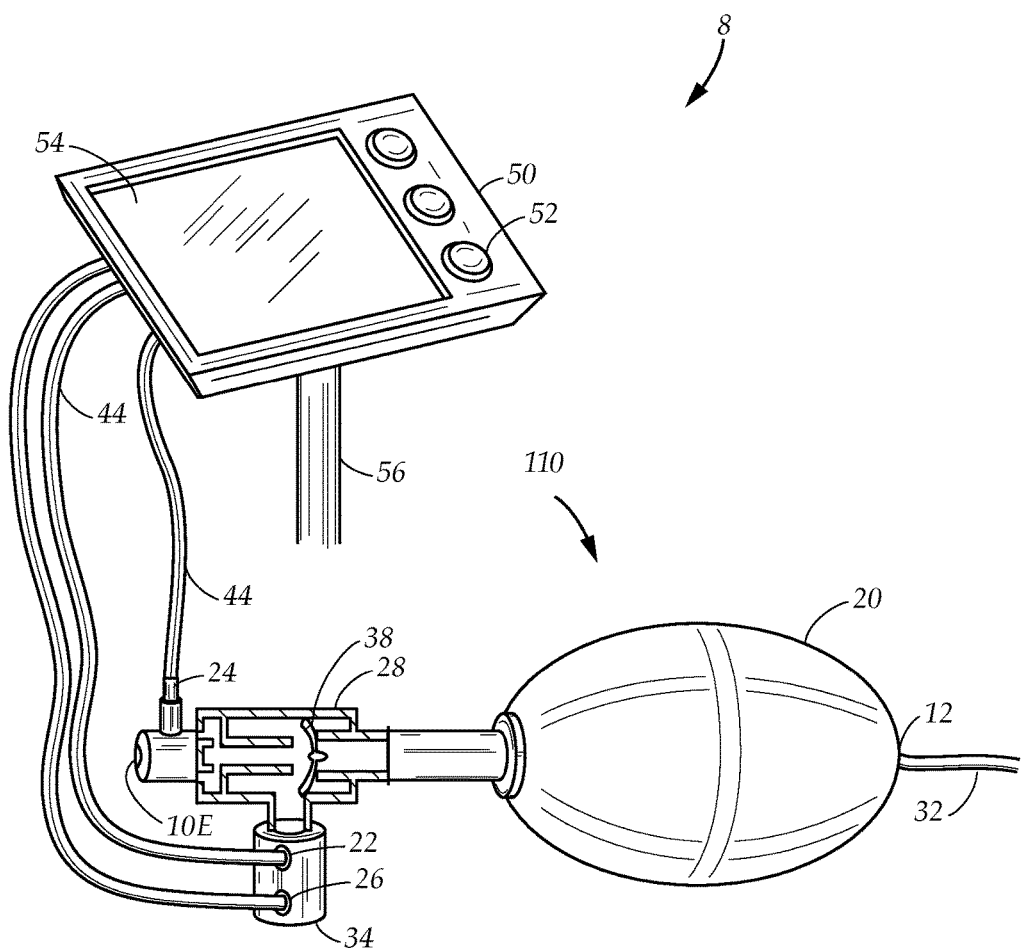
FIG. 4 is a perspective view of another example embodiment of a portable open breathing circuit ventilation device.

FIG. 4 illustrates a monitor 50 coupled to an open breathing circuit 110. The monitor has a display screen 54 for displaying the parameters measured by the sensors. The monitor is coupled to the sensors. In this example embodiment, each said sensor has a lead 44 connecting to the monitor 50. In another example embodiment, tubing operative for conducting air to the monitor connects to the monitor. It is understood by those of ordinary skill that the lead can be tubing, electrical wiring or other means of connecting the sensors to the monitor. The monitor displays on the display screen 54 the measurements for each parameter as the squeezable bag 20 is compressed, manually ventilating a patient. The monitor has internal electronic circuitry and software operative for displaying the measurements in a variety of formats including graphical displays such as curves. The monitor has an internal alarm system operative for sounding an audio alert when a measured parameter measures outside a pre-set range. The monitor has a set of controls 52, shown here as analog dials, as a non-limiting illustration operative for setting said pre-set range and an alert level. In other example embodiments, the controls are digital. Monitors are well known to those of ordinary skill and discussion of further details of the monitor is outside the scope of this disclosure.

The monitor 50 can be mounted on a stand 56 as shown, a wall or can be used independently. The stand 56 is selectively adjustable in height. The monitor can be powered by AC or DC current, the DC current powered by a battery, preferably rechargeable.

In the configuration of the manual open circuit ventilation device 8 in FIG. 4, the gas port is opposite a single-shutter valve 28, allowing connecting tubing 32 for the gas inflow to attach directly to the bag 20. The patient outflow comes through a port 34, the port coupling the open circuit to the patient, either by coupling to a face mask or artificial airway. In this example embodiment, the single shutter valve replaces the pair of valves, the inspiratory valve and expiratory valve, the single-shutter valve functioning as both. In FIG. 4, the valve is open to the expiratory side, the expired gases from the patient passing over the ETCO2 sensor 26 for measurement. Downstream is the TV sensor 24, the three sensors connecting to the monitor by leads 44, the gases flowing to the expiratory side intersection. When the inspiratory gas passes over sensor 22, PAP is measured.

Figure 3:
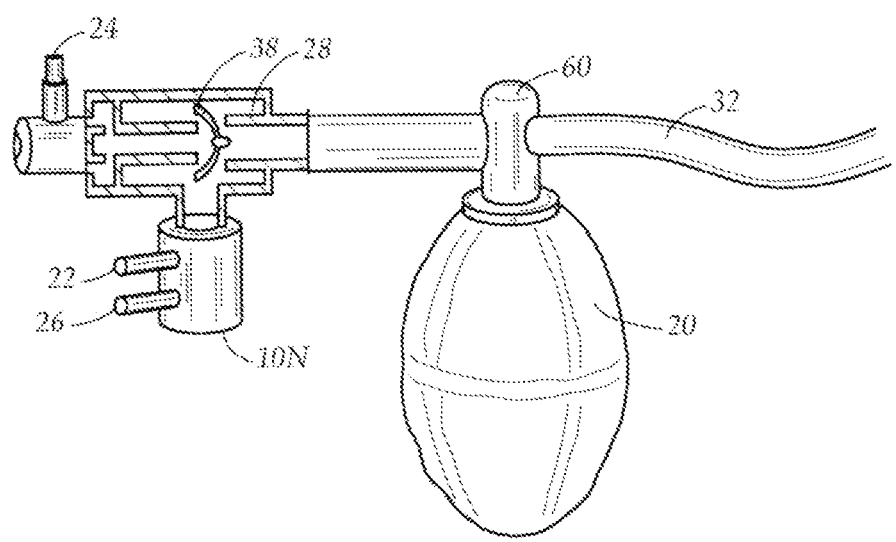
FIG. 3 is a perspective view of a further example embodiment of an open breathing circuit showing a valve in cross-section.

In FIG. 3, in a further example embodiment, the configuration of the open breathing circuit has the connecting tubing 32 for the gas inflow coupled to the squeezable bag 20 through a valve 60. The single-shutter valve 28 is open to the inspiratory side. The single-shutter valve 28 has a shutter 38 that opens the path to the patient via the inspiratory side intersection with positive air pressure provided by squeezing the bag 20. PAP is measured during the inspiratory phase via the PAP sensor 22 and ETCO2 and TV are measured during the expiratory phase via the ETCO2 sensor 26 and the TV sensor 24.

Figure 2:
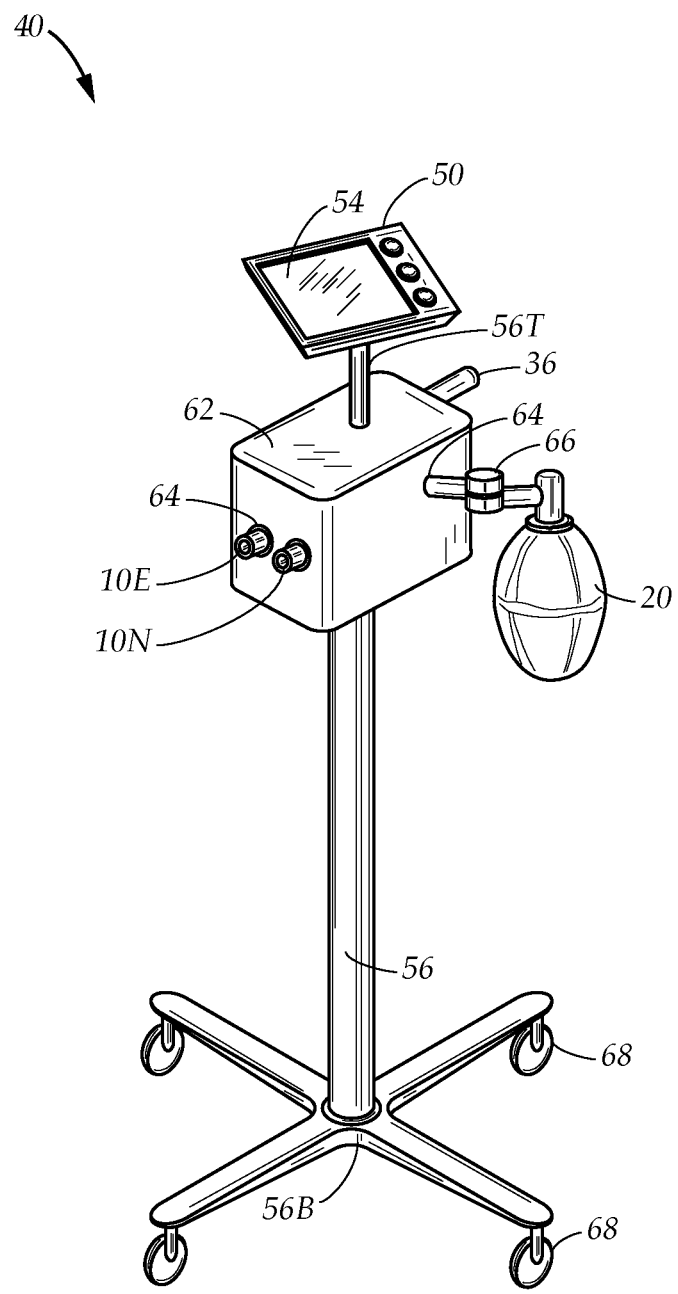
FIG. 2 is a perspective view of the portable closed circuit ventilation system.

FIG. 2 shows portable ventilation system 40 for manually ventilating the patient in clinical applications. The system has the manual closed circuit ventilation device, having the monitor 50 and the closed breathing circuit. The system has a housing 62 having a plurality of openings 64 operative for coupling tubing to the closed breathing circuit. A portion of the closed breathing circuit as described in various example embodiments hereinabove, namely, the valves, tubing, the carbon dioxide absorption canister and sensors, said portion is enclosed in the housing. The squeezable bag 20 of the circuit is external to the housing and is coupled to the circuit by a pivoting joint 66. The expiratory side intersection 10E and the inspiratory side intersection 10N extend through the openings 64 operative for coupling to a ventilation interface such as a mask or an artificial airway. The tubing 36 for the gas inflow extends through another opening.

The system has a portable stand 56, having a top 56T and a bottom 56B, the bottom having wheels 68, the top 56T coupled to the monitor, the monitor on top of the stand external to the housing 62. The housing has the closed breathing circuit coupled to the stand 56 between the top 56T and the bottom 56B. The stand 56 can portably wheel to a patient requiring ventilation. The monitor 50 on the stand displays on the display screen 54, the measurement for each parameter measured by the sensors as the squeezable bag 20 is compressed, manually ventilating the patient, the monitor assuring safe and efficacious manual ventilation by the closed breathing circuit. Further, TV and ETCO2 are measurable while the patient is breathing spontaneous as well.

In one example embodiment, the sensors have leads to the monitor, the leads enclosed by the housing and stand. In a further example embodiment, the sensors are in communication with the monitor through tubing. In other example embodiments, the sensors communicate wirelessly to the monitor.

Referring to FIG. 2, the patient has been sedated undergoing a clinical procedure or surgery. No gaseous anesthesia is administered. The patient is breathing on his own without a traditional anesthesia machine. The patient stops breathing and requires resuscitation. Medical personnel wheel the portable ventilation system to the patient. The closed breathing circuit 10 within the housing is connected via tubing 36 to a source of gas, such as oxygen, and the monitor 50 is turned on. A ventilation mask is placed over the patient's face. The medical personnel squeeze the bag 20, resuscitating the patient while watching the screen 54 where the measurements of TV, PAP and ETCO2 are displayed, adjusting the squeezing of the bag 20 to produce effective ventilation.

The manual closed circuit ventilation device as illustrated in FIG. 1 is made by connecting the manually squeezable bag 20, the carbon dioxide absorption canister 30, the valves, namely the inspiratory valve 14, the expiratory valve 16, and valve 18 and the gas port 12, all in fluid communication via tubing 36. The tubing has the expiratory intersection 10E and the inspiratory intersection 10N for further coupling with a mask or artificial airway. The sensors 22, 24, and the ETCO2 sensor, which is not shown in this illustration, are coupled to the interior of the tubing. The sensors are coupled to and in communication with a monitor.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented a portable manual ventilation device. The disclosure is illustrated by example in the drawing figures, and throughout the written description. It should be understood that numerous variations are possible, while adhering to the inventive concept. Such variations are contemplated as being a part of the present disclosure.

What is claimed is:

1. A portable open circuit ventilation device for manually ventilating a patient, comprising:
   an open breathing circuit having a single-shutter valve configured for coupling to a manually squeezable bag, an outflow port, an inflow port, connecting tubing having an interior, said valve, said outflow port and said inflow port coupled by said connecting tubing and in fluid communication in the open breathing circuit; and
   a plurality of sensors, said sensors operative for measuring a plurality of parameters within the open breathing circuit, said sensors producing a measurement for a parameter, said sensors coupled to said connecting tubing interior of the open breathing circuit, at least one sensor in fluid communication to the outflow port and at least one sensor in fluid communication to the inflow port, said sensors configured for coupling to a monitor.

2. The device as described in claim 1, wherein a monitor having a display screen displays said sensor measurements for the measured parameters as a patient is ventilated in manual mode only, the monitor assuring safe and efficacious ventilation through the open breathing circuit.

3. The device as described in claim 2, wherein the single-shutter valve has a shutter that opens a path to the patient when positive air pressure is provided to the single-shutter valve.

4. The device as described in claim 3, wherein the single-shutter valve is open to an inspiratory side of the open breathing circuit.

5. The device as described in claim 4, wherein the parameters measured by said sensors in the open breathing circuit comprise tidal air volume (TV), peak airway pressure (PAP) and end tidal carbon dioxide concentration (ETCO2), said end tidal carbon dioxide within connecting tubing within the same open circuit as said tidal air volume sensor and said peak airway pressure sensor.

6. The device as described in claim 5, wherein PAP is measured during the inspiratory phase at the inflow port via the PAP sensor and ETCO2 and TV are measured during an expiratory phase at the outflow port via the ETCO2 sensor and the TV sensor.

7. The device as described in claim 5, wherein the outflow port couples to an artificial airway.

8. A portable open circuit ventilation device for manually ventilating a patient in clinical applications, comprising:
- an open breathing circuit having a single-shutter valve selectively coupling to a manually squeezable bag, the manually squeezable bag having an inflow port opposite the single-shutter valve, the open breathing circuit having an outflow port, the open breathing circuit having connecting tubing with an interior, said single-shutter valve, said inflow port and said outflow port coupled by said connecting tubing and in fluid communication in the open breathing circuit;
- a plurality of sensors, said sensors operative for measuring a plurality of parameters within the open breathing circuit, at least one sensor in fluid communication to the outflow port and at least one sensor in fluid communication to the inflow port, said sensors producing a measurement for a parameter, said sensor coupled to said connecting tubing interior; and
- a monitor coupled to said sensors, said monitor displaying said measurements for the measured parameters as a patient is manually ventilated, the monitor assuring safe and efficacious manual ventilation through the open breathing circuit when ventilation is in a manual only mode.

9. The device as described in claim 8, wherein the single-shutter valve has a shutter that opens a path to the patient when positive air pressure is provided by squeezing the manually squeezable bag selectively coupled to the single-shutter valve.

10. The device as described in claim 9, wherein the single-shutter valve is open to an inspiratory side of the open breathing circuit.

11. The device as described in claim 10, wherein the parameters measured by said sensors in the open breathing circuit comprise tidal air volume (TV), peak airway pressure (PAP) and end tidal carbon dioxide concentration (ETCO2), said end tidal carbon dioxide within said connecting tubing within the same open circuit as said tidal air volume sensor and said peak airway pressure sensor.

12. The device as described in claim 11, wherein PAP is measured during the inspiratory phase via the PAP sensor and ETCO2 and TV are measured during an expiratory phase via the ETCO2 sensor and the TV sensor.

13. The device as described in claim 12, wherein the outflow port couples to an artificial airway.

14. A portable open circuit ventilation device for manually ventilating a patient in clinical applications, comprising:
- an open breathing circuit having a single-shutter valve configured for selectively coupling to a manually squeezable bag, an outflow port configured for selectively coupling to a ventilation mask, connecting tubing having an interior, said valve and said port coupled by said connecting tubing and in fluid communication in the open breathing circuit;
- a plurality of sensors, said sensors operative for measuring a plurality of parameters within the open breathing circuit, at least one sensor in fluid communication to the outflow port and at least one sensor in fluid communication to the inflow port, said sensors producing a measurement for a parameter, said sensor coupled to said connecting tubing interior; and
- a monitor, said monitor having a display screen, said monitor coupled to said sensors, said monitor displaying on said display screen said measurement for the measured parameter as a patient is manually ventilated, the monitor assuring safe and efficacious manual ventilation through the open breathing circuit.

15. The device as described in claim 14, wherein the single-shutter valve has a shutter that opens a path to the patient when positive air pressure is provided to the single-shutter valve.

16. The device as described in claim 15, wherein the single-shutter valve is open to an inspiratory side of the open breathing circuit.

17. The device as described in claim 16, wherein the parameters measured by said sensors in the open breathing circuit comprise tidal air volume (TV), peak airway pressure (PAP) and end tidal carbon dioxide concentration (ETCO2), said end tidal carbon dioxide within said connecting tubing within the same open circuit as said tidal air volume sensor and said peak airway pressure sensor.

18. The device as described in claim 17, wherein PAP is measured during the inspiratory phase via the PAP sensor and ETCO2 and TV are measured during an expiratory phase via the ETCO2 sensor and the TV sensor.

\* \* \* \* \*